United States Patent [19]

Gorski

[11] Patent Number: 5,637,466

[45] Date of Patent: Jun. 10, 1997

[54] METHOD OF DETECTING BONE ACIDIC GLYCOPROTEIN-75 AND ITS 50,000 MW FRAGMENT AND ANTIBODIES THEREFOR

[75] Inventor: Jeffrey P. Gorski, Prairie Village, Kans.

[73] Assignee: Curators of the University of Missouri, Columbia, Mo.

[21] Appl. No.: 116,480

[22] Filed: Sep. 3, 1993

Related U.S. Application Data

[63] Continuation of Ser. No. 825,509, Jan. 24, 1992, abandoned, which is a continuation-in-part of Ser. No. 580,790, Sep. 11, 1990, abandoned.

[51] Int. Cl.$^6$ .................................................. G01N 33/53
[52] U.S. Cl. ........................ 435/7.9; 435/7.92; 436/514; 436/528; 436/530; 530/840
[58] Field of Search ............................ 435/7.9, 7.92; 436/514, 528, 530, 540, 811, 813; 530/387.1, 388.2, 395, 828, 840

[56] References Cited

PUBLICATIONS

Gorski et al., "Antibodies Against Bone Acidic Glycoprotein–75 Localize 75K Form to Mineralized Phases of Growth Plate and Bone," in Calcium regulation and Bone Metabolism: Basic and Clinical Aspects; Proceedings of the 10th International Conference on Calcium Regulating Hormones and Bone Metabolism, Eds. Cohn et al., Elsevier Science Publishers, Amsterdam, the Netherlands, 1990, pp. 221–226.

Gorski et al., "Bone Acidic Glycoprotein–75 is a Major Synthetic Product of Osteoblastic Cells and Localized as 75–and/or 50–KDa Forms in Mineralized Phases of Bone and Growth Plate and in Serum", J. Biol. Chem., vol. 265, No. 25, (1990), pp. 14956–14963.

J. Gorski, 1988, J. Biol. Chem., 263:15938–15945, "Isolation of New Phosphorylated Glycoprotein from Mineralized Phase of Bone . . . ".

P. Hauschka et al, 1975, Proc. Natl. Acad. sci., 72:3925–3929, "Direct identification of calcium–binding amino acid, γ–carboxyglutamate . . . ".

J. Termine et al, 1981, Cell, 26:99–105, "Osteonectin, A Bone–Specific Protein Linking Mineral to Collagen".

A. Franzen et al, 1985, in The Chem. & Biology of Mineralized Tissues, pp. 132–141, "Proteoglycans & Proteins of Rat Bone", EBSCO Media, Al.

L. Fisher et al, 1987, J. Biol. Chem., 262:9702–9708, "Purification & Partial Characterization of Small Proteoglycans I and II . . . ".

A. Uchiyama, 1986, Biochem., 25:7572–7583, "Isolation & Chem. Charaterization of the Phosphoproteins of Chicken Bone Matrix . . . ".

L. Fisher et al, 1983, J. Biol. Chem., 258:12723–12727, "Matrix Sialoprotein of Developing Bone".

A. Franzen et al, 185, Bioch J (G.B.) 232:715–724, "Isolation & characterization of two sialoproteins present only in bone calcifid matrix".

C. Prince et al, 1987, J. Biol. Chem, 262:2900–2907, "Isolation, Characterization, and Biosynthesis of Phosphorylated Glycoprotein . . . ".

A. Boskey, 1981, Clin. Orthop, 157:225–257, "Current Concepts of the Physiology and Biochemistry of Calcification".

J. Termine, 1980, J. Biol. Chem. 255:9760–9768, "Properties of Dissociatively Extracted Fetal Tooth Matrix Proteins".

A. Linde et al, 1980, J. Biol. Chem., 255:5931–5942, "Noncollagenous Proteins of Dentin".

U. Laemmli, 1970, Nature, 227:680–685, "Cleavage of Structural Proteins during Assembly of Head of Bacteriophage T4".

K. Campbell et al., 1983, J. Biol. Chem., 258:11267–11273, "Staining of $Ca^{2+}$–binding Proteins, Calsequestrin, Calmodulin, Troponin C . . . ".

T. Shinnick et al., 1983, Annu. rev. Microbiol., 37:425–446, "Sythetic Peptide Immunogens as Vaccines".

Huang, et al., J. Cell Biol. vol 107 p. 3819, (1988).

Turner et al., Endogrinology, vol 127, No. 3, pp. 1346–1351, (1990).

Noda et al., J. Cell Biology vol. 108, pp. 713–718, (1989).

Primary Examiner—Lila Feisee
Assistant Examiner—Susan C. Wolski
Attorney, Agent, or Firm—Kohn & Associates

[57] ABSTRACT

A method of detecting bone acidic glycoprotein-75 (BAG-75) antigen includes the steps incubating a serum or synovial fluid sample with anti-BAG antibody, reacting the incubated sample with a signal generating antibody to the anti-BAG-75 antibody, and detecting the signal as an indication of BAG-75 antigen in the serum. Antibodies for use in the test for detecting BAG-75 antigen in serum and synovial fluid samples includes BAG-75 #3-13 peptide anti-serum, anti-BAG-75 protein anti-serum, and monoclonal antibodies against the BAG-75 protein, the antibodies recognizing the 75,000 molecular weight BAG-75 precursor protein and the 50,000 molecular weight BAG-75 fragment in serum and synovial fluid. Molecular weight assignments are based upon electrophoretic mobilities under denaturing conditions.

5 Claims, 15 Drawing Sheets

METHOD OF DETECTING BONE ACIDIC GLYCOPROTEIN-75 AND ITS 50,000 MW FRAGMENT AND ANTIBODIES THEREFOR

This is a continuation of application Ser. No. 07/825,509 filed on Jan. 24, 1992, now abandoned, which is, in turn, a continuation-in-part of application Ser. No. 07/580,790, filed on Sep. 11, 1990, now abandoned.

TECHNICAL FIELD

The present invention relates to a method of preparing antibodies against bone acidic glycoprotein-75 (BAG-75) which recognize a precursor protein and a metabolic fragment of the precursor protein, the resultant antibodies with the above mentioned specificity, and an analytical method to determine the size and amount of the BAG-75 precursor and metabolic fragment present in serum samples.

BACKGROUND OF THE INVENTION

Bone is a vascularized tissue composed of a cellular and an extra-cellular compartment, the latter of which predominates in terms of volume. Accordingly, bone metabolism is integrally related to the remainder of the body through the vascularization extending therethrough. Osteoblasts and osteoclasts are the major differentiated cells of bone. Most of the non-collagenous proteins of bone, such as bone sialoprotein (SP II), osteopontin and osteonectin have been shown to be synthesized by osteoblast-like cells in culture.

It is generally believed that acidic non-collagenous proteins of bone play a direct role in the processes of cell recruitment and mineralization which occur during coupled resorptive and formative phases of bone turnover.

Applicant has recently isolated a new non-collagenous phosphoprotein from the mineralized phase of rat calvarial tissue, bone acidic glycoprotein-75, referred to as BAG-75. Partial characterization of the glycoprotein revealed a distinctive N-terminal sequence, an Asx and Glx content of 29%, and the presence of 7% (w/w) organic phosphate. Ion exchange chromatography of the 4M guanidine HCl/0.5 MEDTA extracts of rat calvaria show that BAG-75 copurifies with small bone proteoglycans. This confirms the very acidic character of the glycoprotein. Although exhibiting nonidentical amino acid compositions, BAG-75 was found to share a limited sequence homology with osteopontin.

Other non-collagenous proteins have recently been studied. Studies have been conducted on osteocalcin, osteonectin, SP II, phosphoproteins, and osteopontin as possible regulators of de novo calcium hydroxyapatite formation and of crystal growth. The specific role of these individual non-collagenous proteins in bone matrix deposition and mineralization remains uncertain, possibly due to the existence of redundant, compensating factors.

The present invention relates to the discovery of detectable BAG-75 antigen in serum and very likely in synovial fluid. An immunoassay is carried out on blood serum using antibodies which selectively bind to BAG-75 or its 50,000 molecular weight fragment.

SUMMARY OF THE INVENTION

In accordance with the present invention, there is provided a method of detecting bone acidic glycoprotein-75 (BAG-75) antigen, the method including the steps of incubating a serum or synovial fluid sample with anti-BAG-75 antibody, forming BAG-75 antigen/antibody complexes and detecting the antigen/antibody complexes. The signal is detected as an indication of BAG-75 antigen in the serum or synovial fluid sample.

The present invention further provides antibodies for use in a test for detecting BAG antigen in serum and synovial fluid samples. The antibodies include BAG-75 #3-13 peptide anti-serum, an anti-BAG-75 protein anti-serum and monoclonal antibodies against the BAG-75 protein, the antibodies recognizing the 75,000 molecular weight BAG-75 precursor protein and the 50,000 molecular weight BAG-75 fragment in serum and synovial fluid. Molecular weight assignments are based upon electrophoretic mobilities under denaturing conditions.

FIGURES IN THE DRAWINGS

Other advantages of the present invention will be readily appreciated as the same becomes better understood by reference to the following detailed description when considered in connection with the accompanying drawings wherein:

FIG. 1 shows comparative ELISA (enzyme-linked immunosorbent-assay) titration data of bone acidic glycoprotein 75 with anti-peptide and anti-protein sera;

FIG. 2 shows the reactivity of purified bone proteins and calvarial extracts with anti-BAG-75 protein anti-serum wherein micrograph A shows samples that were electrophoresed on 7.5% mini-gels, transblotted onto cationic nylon membranes, Individual lanes: BAG-75 (1×) 5 ug; BAG-75 (4×), 20 ug; Calv G/E, guanidine HCl/EDTA extract of calvaria previously extracted with just guanidine HCl; Calv G, initial guanidine HCl extract of calvaria; OP (osteopontin), 10 ug; SP II (bone sialoprotein), 10 ug; and PGI/II (small proteoglycans I and II), 10 ug. B. samples of purified bone acidic glycoprotein-75 were electrophoresed on mini-gels before or after long-term storage at 4° C., gel lanes were then either processed for immunoblotting or stained with Stains-All™ ({1-ethyl-2[3-(1-ethylnaphtoh[1,2-d]thiazolin-2-ylidene)-2-methylpropenyl]naphtho[1,2-d] thiazolium bromide} Aldrich Chemical Catalog, Milwaukee, Wis., Phone 1-800-588-9160). Lane 1. pattern before storage (stained); lane 2, pattern after storage (stained): lane 3, pattern after storage (immunoblot);

FIG. 3 shows ion exchange chromatography of total G/E extract of rat calvaria on DEAE-Sephacel. A. profiles of optical density (280 nm) and Alcian Blue dye binding (620 nm) measurements. B. ELISA analyses for bone acidic glycoprotein-75 and for osteopontin. C. polyacrylamide gel electrophoresis of selected column fractions on 7.5% mini-gels. Gels were stained with Stains-All™ or with Coomassie Blue dye as noted above gel lanes. Molecular weight estimates are empirical and based upon a comparison with globular protein standards co-electrophoresed with unknown.

FIG. 4 is a comparison of immunoblotting results obtained with DEAE-Sephacel column fractions and either cationic nylon or with nitrocellulose membranes. Selected column fractions from FIG. 3 were electrophoresed on 7.5% mini-gels, transblotted and antigens visualized. A. immunoblotting with cationic nylon membrane and with anti-BAG-75 protein antiserum. B. immunoblotting with nitrocellulose membrane and with anti-BAG-75 protein antiserum. C. negative control blot with cationic nylon membrane and with preimmune serum;

FIG. 5 is an analysis of the level of BAG-75 and/or molecular weight=50,000 fragment in rat serum as a function of early post-natal development. The ages of donor rats are noted at the bottom of respective gel lanes; 5 microliters of serum was analyzed in all cases with BAG-75 antigen specific immunoassay. Positions of BAG-75 and molecular weight=50,000 fragment are noted on the figure;

FIG. 6 is a photomicrograph of antibodies against rat BAG-75 peptide #3-13 detecting human BAG-75 and molecular weight=50,000 fragment forms in serum. Human serum was analyzed at the two and five microliter level; a positive control rat serum sample was also included. Positions of BAG-75 and molecular weight=50,000 fragment are noted on the figure;

FIG. 7 is a photomicrograph showing serum from osteosarcoma bearing rats which is enriched in BAG-75 (molecular weight=75,000). Identities of serum samples are noted at the bottom of the figure; molecular weight estimates are noted on the figure and denote a major increase in antigen content of BAG-75 in tumor bearing rat sera;

FIG. 8 is a chart showing that ovariectomy of rats causes a rapid 3-fold elevation in serum of the molecular weight= 50,000 fragment of BAG-75. Identity of experimental groups is denoted as intact (control); OVEX (ovariectomized); and, OVEX+E (estrogen supplemented ovariectomized rats). The average areas of the fragment band after immunostaining and densitometry are presented on the figure along with respective standard deviations.

DETAILED DESCRIPTION OF THE INVENTION

Figure 1:
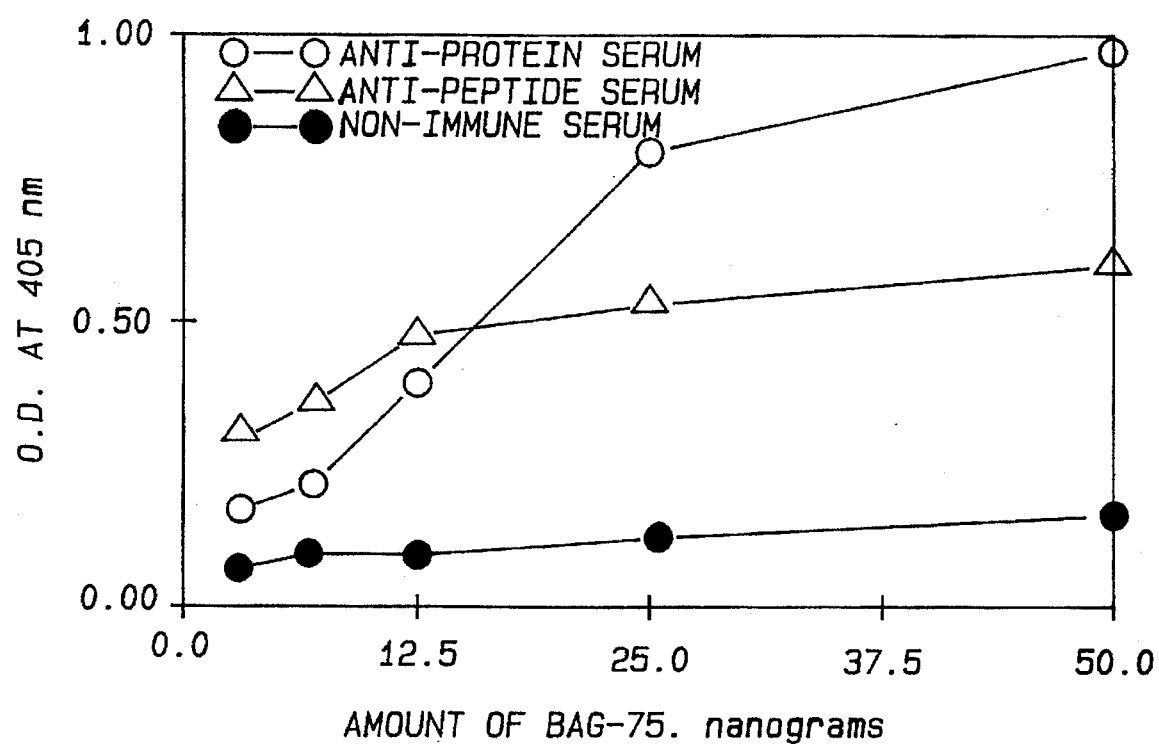

The isolation and characterization of the BAG-75 antigen from the mineralized compartment of rat skull bone has been previously reported. Although restricted in its synthesis and distribution to extracellular mineralized matrix of calcifying tissues, a Mr=50 kDa fragment of BAG-75 was detected in rodent and human serum, as well as in calcified tissue extracts. The presence of this fragement in serum, especially human serum, possesses significant potential in light of the fact that a need exists for additional, more specific serum markers of bone turnover in diagnosis and monitoring of osteoporotic patients. The present inventors have produced two kinds of polyclonal anti-serum which were found to recognize specifically BAG-75 and a smaller metabolic breakdown fragment in extracts of calcified tissues.

Purification of Proteins

Preparation and extraction of rat calvaria with 4M guanidine-HCl 4M guanidine-HCl/0.5M EDTA containing inhibitors; and BAG-75 isolation were performed as described by Gorski and Shimizu. Purification of Rat Calvarial BAG-75 and SP II-Two month old Sprague-Dawley rats were killed; calvaria were removed immediately and cleaned of soft tissue and blood. Unless noted, all procedures were carried out at 4° C. Ten to twenty calvaria (2.9–5.8 g, wet weight) represented the starting material for a typical preparation. Following removal of cartilaginous sutures, calvarial tissue was cut into small pieces, washed five times with Buffer A consisting of 0.05M Tris acetate buffer (pH 7.4), containing 0.1M$\Sigma$-amino-n-caproic acid. 0.005M benzamidine hydrochloride, 0.001M phenylmethyl Sulfonyl fluoride, 0.001M p-hydroxymercuribenzoate, 1 mg/liter soybean inhibitor, and 5 mg/liter pepstatin, freeze dried, and weighed. Dried tissue was extracted for 72 h with Buffer A containing 4M guanidine hydrochloride. Insoluble residue was pelleted by centrifugation at 10,000 rpm for 30 min. and re-extracted for 72 h with Buffer A containing 0.5M EDTA and 4M guanidine hydrochloride. The second extract was subjected to DEAE-Sephacel chromatography in 0.1M sodium acetate buffer (pH 5.6), containing 6M urea and 0.2% CHAPS; elution was affected with a linear gradient of 0.1–2.5M sodium acetate. Fractions were analyzed directly for protein (absorbance at 280 nm). For sialic acid analysis, aliquots were concentrated in Centricon 10 devices (Amicon Corp.) exchanged into 0.05M Tris acetate buffer (pH 7.5), hydrolyzed for 1 h at 80° C. in 0.1M sulfuric acid, and analyzed by a micro-version of the thiobarbituric acid procedure of Warren. Unknowns were compared to a standard curve constructed with synthetic N-acetylneuraminic acid (Sigma). For glycosaminoglycan chain analysis, 0.15 ml of fractions were digested with proteinase K (50 µg/tube) at 37° C. for 16 h, and digests were exchanged into 0.001M Tris acetate buffer (pH 7.5) and then assayed via a micro-version of the Alcian blue dye binding method of Whiteman. Fraction aliquots were also boiled in the presence of sodium dodecyl sulfate, dialyzed against 0.05% SDS in water, lyophillized to dryness, and electrophoresed on 3–20% gradient sodium dodecyl sulfate-polyacrylamide slab gels prepared with solutions of the Laemmli gel system. Bone proteins were visualized after staining with Stains-All dye and/or Coomassie Brilliant Blue Dye.

The combined BAG-75 and proteoglycan pool was then chromatographed on hydroxyapatite in 0.01M Tris phosphate buffer (pH 7.4), containing 7M urea. A linear gradient of 0.01–0.5M sodium phosphate resolved each of the two components into separate peaks. Columns were monitored continuously at 280 nm; individual fractions were analyzed for sialic acid, for polypeptide composition by SDS-polyacrylamide gel electrophoresis, and/or for glycosaminoglycan chain content as described above. Fractions of interest were combined and the pools frozen at −70° C. until ready to use. The N-terminal sequence of the first fifteen residues of BAG-75 was determined chemically. A single sequence was obtained with leucine as the N-terminal residue. The entire sequence deduced was Leu-Pro-Val-Ala-Arg-Thr-Gln-Asn-Thr-Glu-Glu-Glu-Glu-(Glu/Asp)-(Glu/Asp)-, with the last two cycles yielding glutamic acid and aspartic acid in about equal quantities (Gorski et al., 1988, pp. 15938–15939). Separate side fractions were used to purify rat osteopontin, sialoprotein, and small proteoglycans.

Preparation of Anti-BAG-75 #3-13

A cysteinyl derivative of BAG-75 peptide #3-13 was synthesized by Immuno-Dynamics, Inc., La Jolla, Calif. according to the inventors directions and M-maleimidobenzoyl-N-hydroxysuccinimide conjugated by an ester coupling step to bovine serum albumin, ovalbumin or keyhole limpet hemocyanin.

Antibody Production

A rabbit was immunized with mashed SDS-PAGE gel slices containing purified BAG-75 (Mr=75 k) stained band. Booster injections in incomplete Freund's adjuvant were made regularly until a useable antibody titer was reached. Rabbits were injected initially with individual peptide conjugate suspended in Freunds' complete adjuvant. Booster injections in incomplete adjuvant were made every 1–3 weeks until a useable antibody titer was reached. Useable antisera were obtained with rabbits injected with serum albumin or ovalbumin peptide #3-13 conjugates which cross-reacted with BAG-75 protein. No antibodies could be produced with the respective keyhole limpet hemocyanin conjugate.

No cross reactivity was found with other purified acidic bone matrix proteins, including osteopontin, bone sialoprotein, and bone proteoglycans I and II. To characterize the reactivity of these two antisera, extracts of kidney, liver, lung, heart, spleen, brain, growth plate, and calvaria bone were made. Immune reactivity was only observed in extracts of calcified tissues, growth plate, and bone. Even in these tissues, it was necessary to demineralize the tissue to release the 75,000 molecular weight form of BAG-75, although the 50,000 molecular weight fragment was detectable in extracts in the absence of demineralization. This result could be due to the lower negative charge density of the 50,000 molecular weight fragment as compared to the 75,000 molecular weight precursor. In this way, the fragment does not exhibit the same strong attraction to the hydroxyapatite crystals of calcified tissues and thereby a portion would be extractable by non-demineralizing media.

These results led the inventors of the present invention to search for BAG-75 or its fragment in blood serum. Such bone non-collagenous proteins have not previously been detectable in serum or synovial fluid. As set forth below, applicants successfully demonstrate the 50,000 molecular weight fragment of BAG-75 in rat serum with anti-BAG-75 peptide #3-13 antibodies. As set forth below in detail, applicants research utilized several types of antibody dependent methods: ELISA, RIA (radioaminoassay), and immunoblotting or Western blotting.

ELISA Assays

Two hundred microliters of test antigen were added to microtiter wells in duplicate and each serially diluted across a twelve well row with phosphate-buffered saline containing 0.02% azide and adsorption of antigen allowed to proceed for 16 hours at 37° C. Analysis of each test antigen at a total of 12 different dilutions ensured that optical density values in the linear range were obtained for some dilutions of all test antigens in a given assay run, which proved particularly useful in comparative studies with column fractions. Two sets of plates were set up per run; one set was incubated with primary antibodies and a second set was incubated with preimmune rabbit serum (negative control). Several positive control wells were also included in each assay (i.e. anti-albumin antibodies with albumin protein adsorbed to plate). Wells were washed with phosphate-buffered saline containing 0.05% Tween 20 and then incubated with 100 μl of phosphate-buffered saline containing 1% ovalbumin for two hours at 37° C. to block residual binding sites. Plates were then washed and wells incubated with primary antiserum or preimmune serum (generally 1/200 to 1/500 dilution) for one hour at 37° C. After removal of primary antiserum, wells were washed five times prior to addition of 100 μl of horseradish peroxidase conjugated second antibody (1/500). Following a one hour incubation at room temperature in the dark and removal of unbound second antibody, colorimetric detection was accomplished by incubation for 30–90 minutes in the presence of 100 μl of 0.052M sodium phosphate buffer (pH 5.2) containing 0.024M citrate, 0.182M ABTS [2,2'-azinobis(3-ethylbenzthiazolinesulfonic acid)]. and 0.09% hydrogen peroxide. Optical density measurements were made at 405 nm with a microtiter plate reader.

Western Blotting

Column Fractions—Aliquots (2 ml) of column fractions from a DEAE column separation of a total 4M guanidine HCl/0.5M EDTA extract of calvaria were boiled in the presence of 0.1% sodium dodecyl sulfate, dialyzed against two changes of 0.05% sodium dodecyl sulfate, and lyophilized separately. After solubilization and boiling in 8M urea containing inhibitors and an excess of dithiothreitol, equal volumes of fractions were electrophoresed on duplicate sets of 7.5% polyacrylamide mini-gels at 100 volts for one hour at 4° C. The first set of gels was transblotted onto nitrocellulose paper for one hour at 100 V in cold transphor buffer containing 25 mM tris-glycine (pH 8.3) and 20% methanol. The second set was transblotted onto positively charged nylon membranes (zetaprobe, Bio-Rad) for two hours at 100 V. After blotting, gels were stained in Stains-All™ dye to confirm protein transfer. Blots were processed for immunodetection. Molecular weight estimates of immunoreactive bands were made by reference to Coomassie Blue pre-stained globular standards co-electrophoresed and transblotted along with fractions.

Rabbit antibodies were raised separately against protein conjugates containing N-terminal peptide residues (residues 3–13) of BAG-75, as well as against gel slices containing BAG-75 protein. The peptide sequence #3-13 was chosen because it represents a decamer, the minimum preferred size for peptide antigens, and comprises the most distinctive sequence among the fifteen known residues. Residues 3 and 13 are identical with similar positions in rat osteopontin.

As demonstrated by the titration study illustrated in FIG. 1, both types of antisera recognize purified BAG-75 protein (molecular weight=75,000) in ELISA assays. Whereas nonimmune serum gave a background response over the entire range of antigen tested, the anti-peptide and anti-protein sera gave rise to a detectable antigen-dependent reaction from 3 ng to more than 50 ng of input protein. Other results (not shown) indicated that anti-peptide antibodies reacted with BAG peptide #3-13 coupled to a nonhomologous protein conjugate and that immunoreactivity could be blocked by the addition of free BAG peptide #3-13.

Figure 2A:
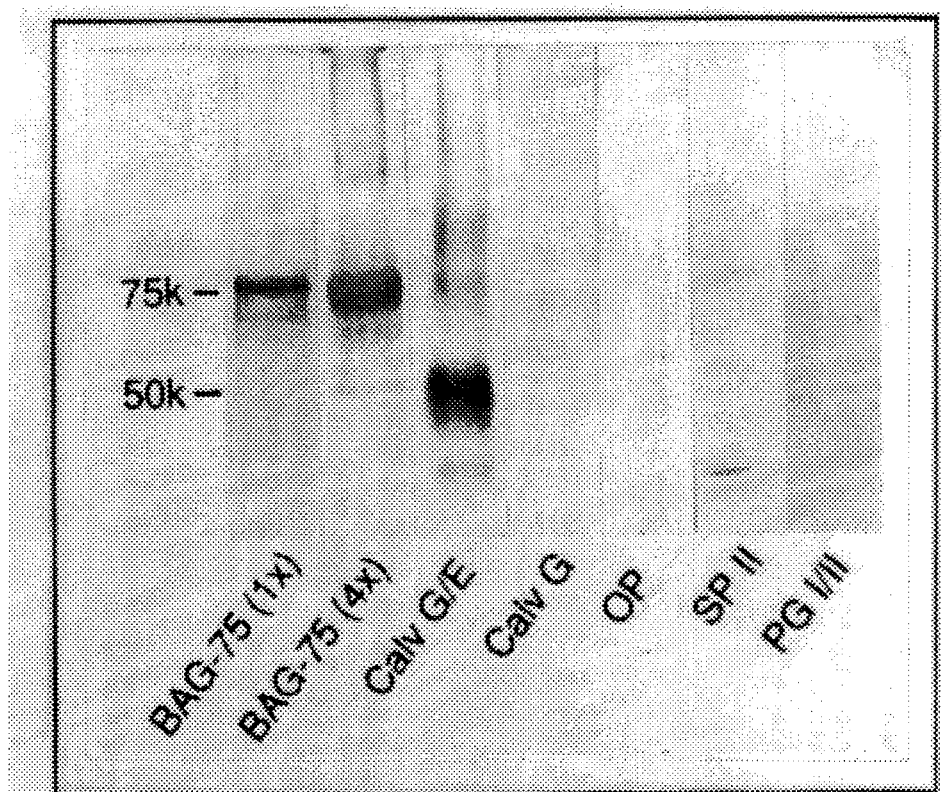
Figure 2B:
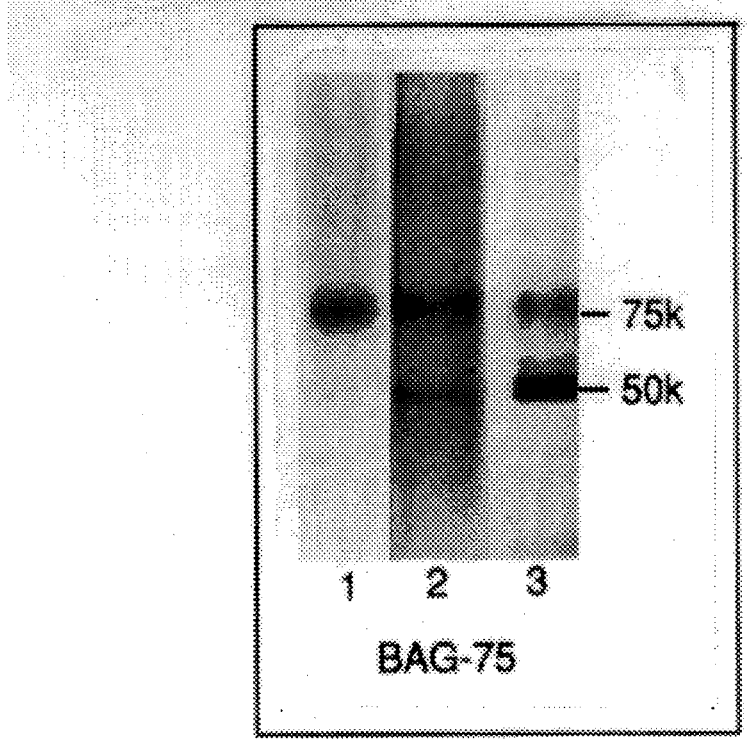

Anti-BAG-75 protein serum was analyzed by Western immunoblotting with a series of purified bone matrix proteins and tissue extracts in order to assess its specificity. FIG. 2A depicts the results of blotting with 5 and 20 ug of purified BAG-75. A major molecular weight=75,000 band and two slightly smaller forms were observed at both levels. Only trace recognition of other components occurred at the higher load. A molecular weight=50,000 fragment appeared upon prolonged storage of some preparations of purified BAG-75. This fragment, detected weakly with Stains-All™ dye, is reactive with anti-BAG-75 protein antibodies, frequently exhibiting two closely spaced bands (FIG. 2B).

In contrast, purified rat bone sialoprotein, osteopontin, and small bone proteoglycans I (biglycan) and II (decorin) were found to be unreactive with anti-BAG-75 protein antibodies (FIG. 2A), under conditions where each is easily detected by its own antiserum. BAG-75 antigenicity in calvarial extracts was found almost exclusively in the 4M guanidine HCl/0.5M EDTA extract, implying a requirement for decalcification for its release. Calvarial immunoreactivity was comprised of a major, broad band at molecular weight=50,000, with other bands at molecular weight=75,000 and at molecular weight=160,000 (FIG. 2A). Thus, anti-BAG-75 protein serum, although not cross-reactive with potential contaminants osteopontin, bone sialoprotein, and small proteoglycans, delineates two other sized protein bands associated with a mineralized phase of rat calvaria.

Figure 3A:
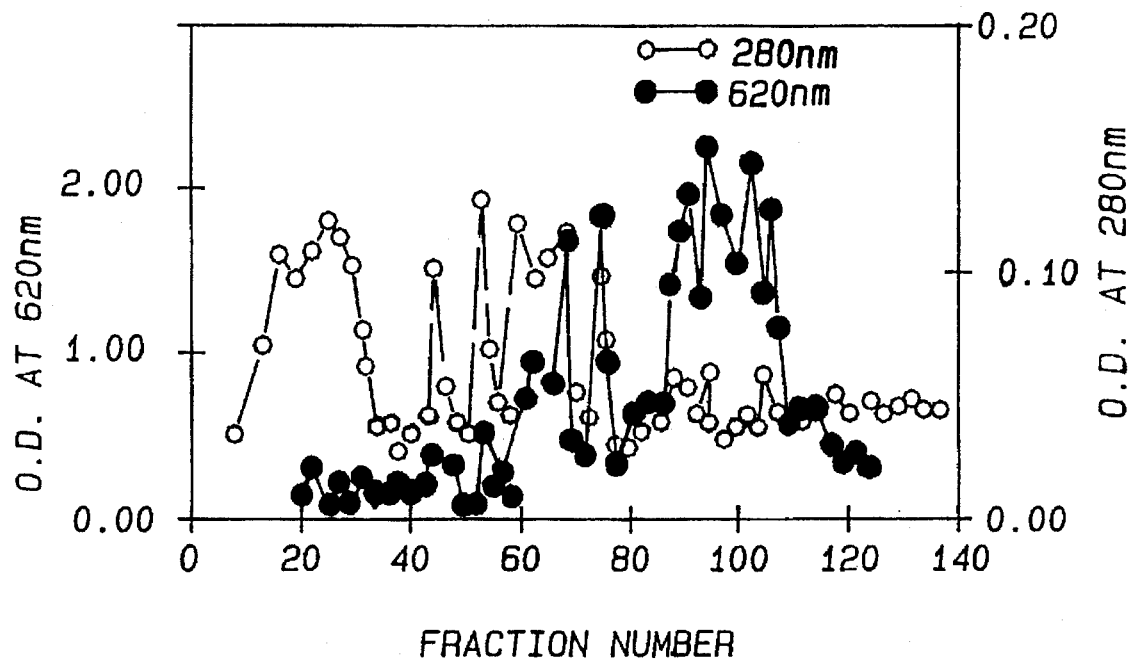

In view of the recognition of several calvarial protein bands in addition to the previously isolated molecular weight=75,000 form of BAG-75, applicant next analyzed fractions from a DEAE-Sephacel separation of a total G/E extract (4M guanidine HCl, 0.5M EDTA) of calvaria. Immunoreactivity was be correlated directly with the elution profiles of individual calvarial proteins, whose identity could be established by independent means. For reference, the optical density profile at 280 nm is depicted in FIG. 3A along with that for Alcian Blue dye binding by acidic macromolecules. The gel electrophoretic pattern of every tenth fraction is presented in FIG. 3C. Only components present in fractions after 60 exhibited appreciable binding of cationic dyes; osteopontin (molecular weight=56,000), bone sialoprotein (molecular weight=72,000), and proteoglycans I and II (molecular weight=130,000 and 250,000) were detected in fractions 70–80, 80, and 90–100, respectively.

Figure 3B:
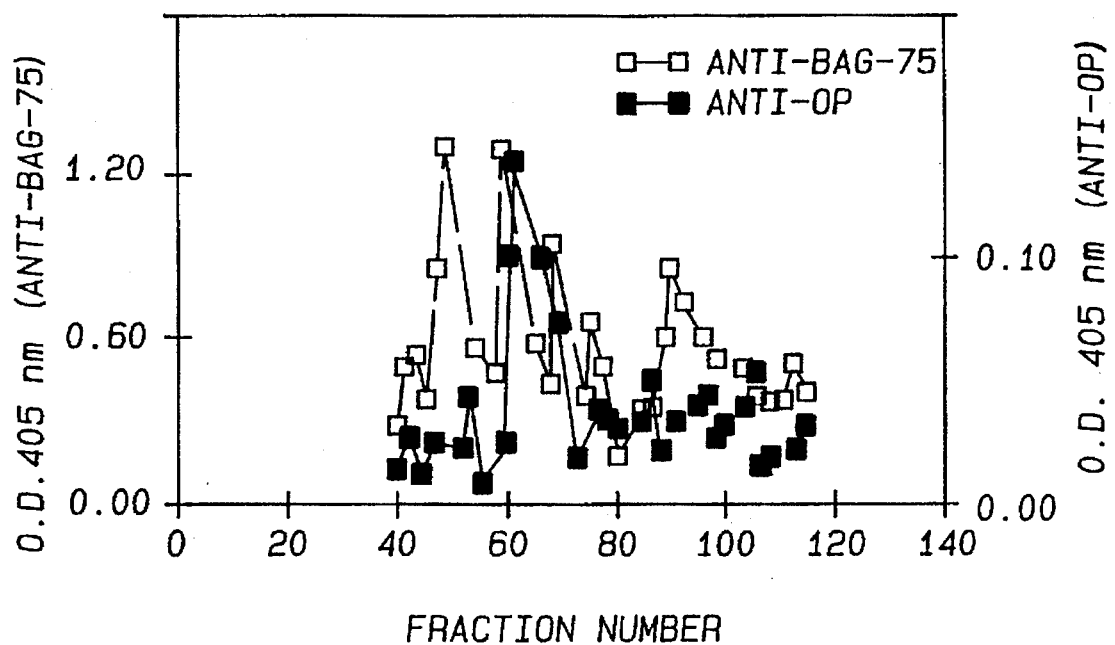

Binding of anti-BAG-75 protein antibodies was monitored both by ELISA and by Western blotting on selected fractions: three major peaks of immuno-reactivity were observed at fractions 54,62, and 92 (FIG. 3B). Minor immune recognition occurred at fractions 46,68 and 74, each of which represents a major peak of protein elution (A 280 nm). In view of the potential cross-reactivity of osteopontin with anti-BAG-75 antibodies due to a limited sequence homology, fractions were analyzed with monoclonal anti-osteopontin antibodies. However, a single, separate peak of immunoreactivity was obtained at fraction 64. A lack of direct correspondence of the osteopontin and BAG-75 ELISA profiles further supports a lack of immunological relatedness between these glycoproteins.

Figure 3C:
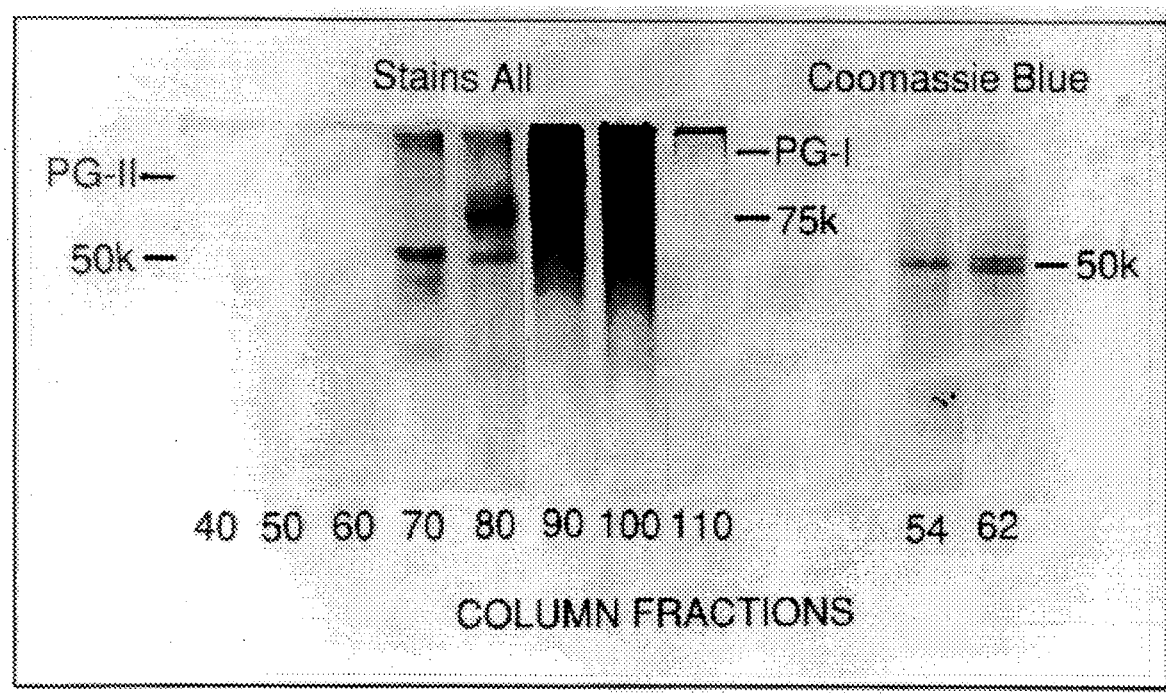
Figure 4A:
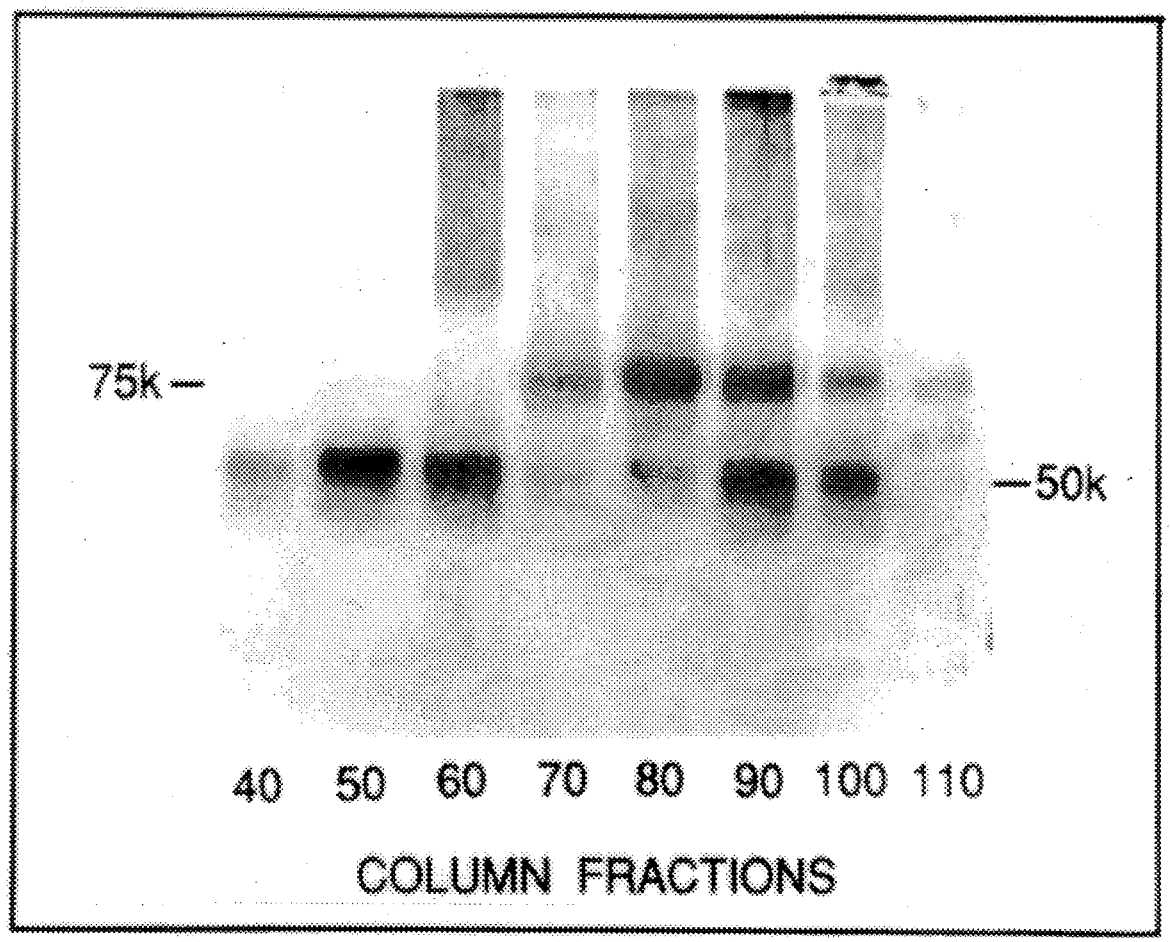
Figure 4B:
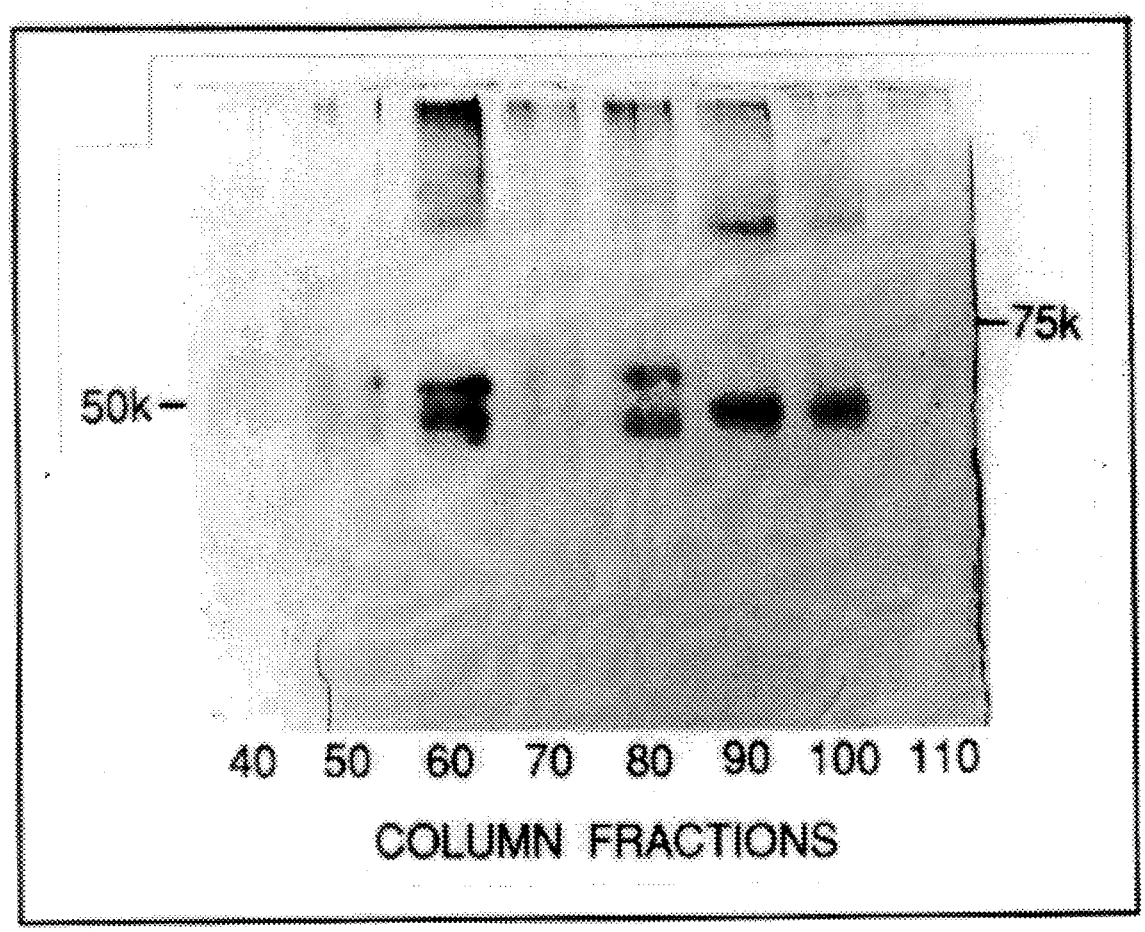
Figure 4C:
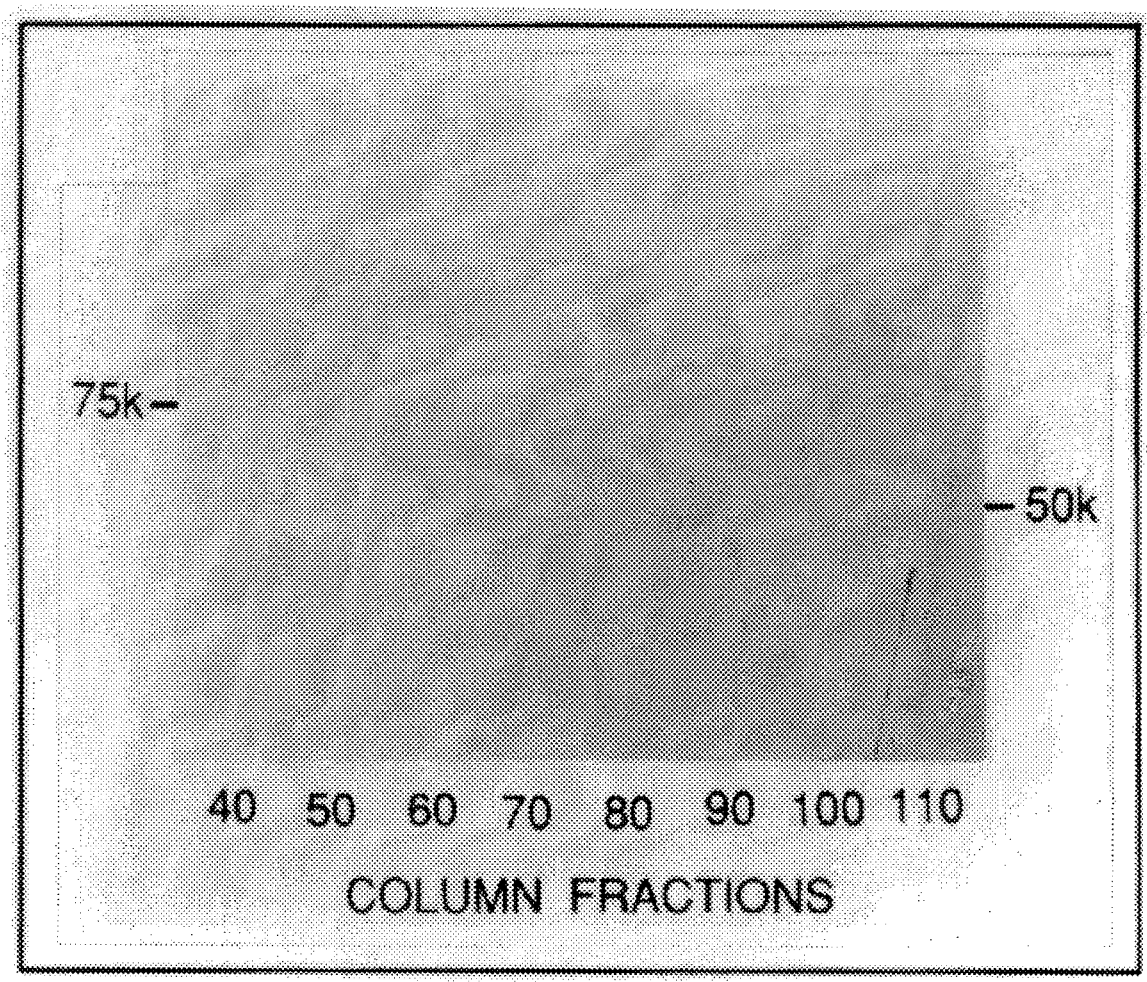

Results of Western blotting with column fractions on cationic nylon and nitrocellulose membranes are presented in FIGS. 4 A and B; a negative control with normal rabbit serum is shown in FIG. 4C. Comparison of results with these membranes yields several interesting findings. First, the molecular weight=75,000 form of BAG-75 can be detected only with positively charged membranes and is restricted to fractions 70–100, the co-elution position for small bone proteoglycans and for BAG-75 (FIG. 3C). Second anti-BAG-75 protein antibodies recognize two closely spaced bands of approximately molecular weight=50,000 in fractions 40–60 and 80–100. The presence of a molecular weight=50,000 immunoreactive band in fractions 80–100 is believed to have been produced by cleavage of BAG-75 (molecular weight=75,000) prior to sodium dodecyl sulfate-polyacrylamide gel electrophoresis and subsequent to DEAE chromatography. Reference to FIG. 3C indicates that one and two polypeptides of molecular weight=50,000 represent the predominant protein species in fractions 54 and 62, respectively; only the smaller of the doublet bands transferred to cationic nylon membranes (FIG. 4A). These findings (FIG. 4, A and B) demonstrate that the major stained polypeptide components in fractions 54 and 62 exhibit immunoreactivity with anti-BAG-75 protein antibodies. Taken together, the data suggests that anti-BAG-75 protein antibodies recognize the previously characterized molecular weight=75,000 form of BAG-75, as well as two smaller species of approximate molecular weight=50,000. The latter represents the major antigenic forms in calvarial extracts. Another immunoreactive band observed in total G/E extracts (molecular weight=160,000) (FIG. 2A) was not detectable in column fraction blots suggesting it may be an aggregate of BAG-75 or molecular weight=50,000 proteins arising during processing of electrophoresis.

Each of the above methods demonstrate that two antigenic forms of the BAG-75 protein are present in tissues and serum, that is the BAG-75 having a molecular weight of 75,000 and a 50,000 molecular weight fragment. Thusly, utilizing ELISA and RIA methods, one can derive a sum of antigenic reactivity with a given sample, whereas Western blotting permits detection and quantitation of each antigenic form individually. This is due to the fact that the 50,000 molecular weight fragment and the BAG-75 can be separated by electrophoresis and then transferred directly to a membrane surface prior to immuno-detection. On the basis of this rationale, Western blotting was used as the primary method for analysis of serum. It is very likely and most highly predictable that monoclonal antibodies can be developed which are specific for BAG-75 antigenic form as the analysis generally used antisera which react with both antigenic forms.

Critical to the processes are the use of two types of membranes as surfaces upon which to transfer electrophoretically separated proteins. Nitrocellulose and cationic membranes are used. Applicant previously showed that the cationic paper was necessary to be able to capture the BAG-75 form. When cationic membranes were used with rat serum samples, applicants found that only the 50,000 molecular weight fragment was detected with anti-BAG-75 protein antibodies. Applicants have evidence that the reason for this is that the BAG-75 form, although present in serum also, is not retained by the membrane due to the larger molar excess of serum albumin as compared to the BAG-75 present in serum. Albumin is similar in size to BAG-75 and competes effectively for the limited surface area available. This conclusion was complicated by the fact that the cationic membrane works well for immunodetection of BAG-75 from tissue to extracts. Anti-peptide #3-13 antibodies gave only background reactivity with rat serum samples transferred to cationic membranes. Since the epitope recognized is quite acidic and small, applicants reasoned that this site is covered up when BAG-75 of the 50,000 molecular weight fragment binds to cationic membranes.

When serum is electrophoretically separated and then transferred to nitrocellulose, applicant found that the anti-peptide #3-13 antiserum detected both the 50,000 molecular weight fragment and the BAG-75. The latter, more acidic component was observed both on the front and backside of the porous membrane. Anti-BAG-75 protein antibodies exhibited similar reactivity with the 50,000 molecular weight fragment and the BAG-75 in serum.

Since only bone sialoprotein, osteocalcin, and BAG-75 have been shown thus far to be proteins with a predominantly restricted distribution to calcified tissues, there is little precedent for the finding of BAG-75 and the 50,000 molecular weight fragment in serum.

Procedure for the Preparation of Monoclonal Antibodies

Monoclonal antibodies to BAG-75 would allow production of antibodies that were selected for the BAG-75 precursor form versus those reactive with both the precursor and the 50,000 molecular weight fragment. The method of selection is critical. Applicant would rely upon ELISA assays in which clones would be screened for binding to both precursor and fragment. Cleavage of BAG-75 to yield the 50,000 molecular weight fragment indicates that only a portion of the linear sequence of the precursor is represented in this fragment. As a result, it is straight forward and highly likely to suggest that monoclonal antibodies against precursor specific sequences can be produced by injecting mice with either peptides representing such sequences (obtained through ongoing cDNA cloning efforts) or by injecting BAG-75 and selecting for monoclonal antibodies reactive only with BAG-75 and not the 50,000 molecular weight fragment. It is possible that cleavage of the BAG-75 (Mr=75,000) to Mr=50,000 fragment may be accompanied by conformational changes in the latter. If so, it may be possible to produce monoclonal antibodies which recognize only the Mr=50,000 fragment. Such clones would be detected as those reactive with Mr=50,000 fragment, while not reactive with the Mr=75,000 precursor (BAG-75).

The following studies present additional data showing the clinical applicability of applicant's specific immunodiagnostic test for the BAG-75 and/or 50,000 molecular weight fragment in serum. The following studies were all obtained with the anti-BAG-75 #3-13 peptide antiserum. Of course, such results are highly predictable for monoclonal antibodies as discussed above.

Figure 5:
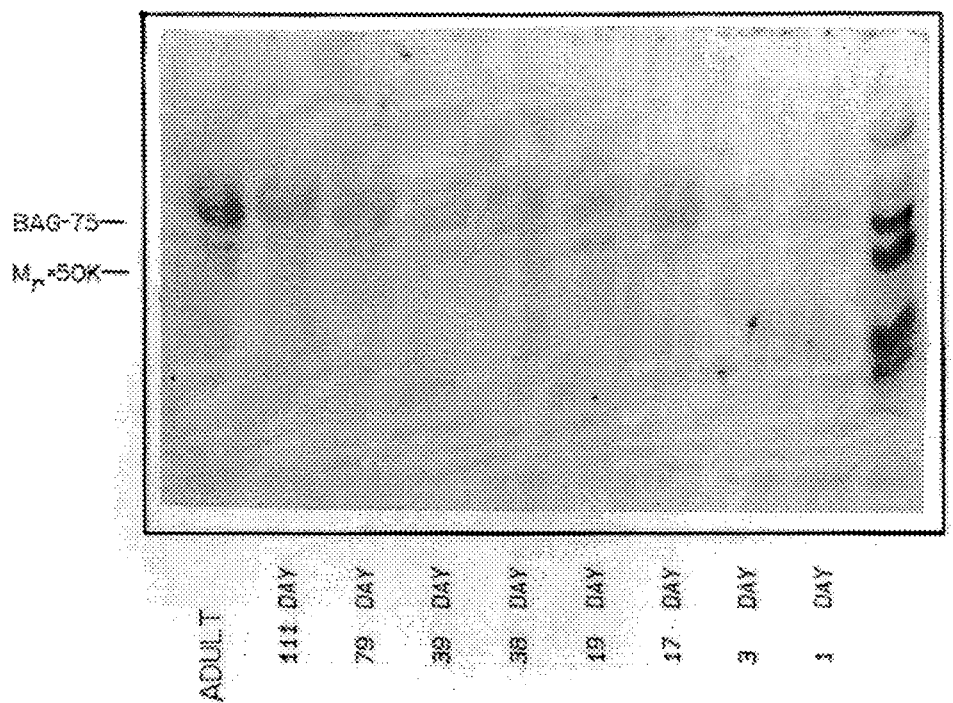

Analysis of the Level of BAG-75 and/or Molecular Weight=50,000 Fragment in Rat Serum As a Function of Early Post-Natal Development Much interest currently revolves around attempts to devise analytical assays to measure materials in serum which reflect the status of bone metabolism for use in diagnosis and treatment of metabolic bone diseases like type I osteoporosis or bone tumors. In order to have a baseline upon which to estimate disease related changes in BAG-75 antigens in serum, applicant have investigated the effect of early development upon these parameters. FIG. 5 depicts the outcome of Western blotting assays of five microliters of rat sera from animals ages 1 day to 111 days, and in an adult. The intensity of the spot is indicative of the amount of antigen present over the range of response observed. All animals were from the same litter and similar results were obtained with two separate litters.

Both BAG-75 (molecular weight=75,000) and molecular weight=50,000 fragment are detected on nitrocellulose membranes. The amount of the former is greater in all ages tested (FIG. 5). The level of BAG-75 antigen is seen to vary somewhat across this age range exhibiting peaks at 17 days and then again in the adult. The mechanism responsible for these changes is presently unknown, but applicant's findings show that the under normal aging conditions the level of BAG-75 is not static and may need to be controlled for with respect to age matched controls. The peak at 17 days may reflect overall bone synthetic rate since this is the time at which the ratio of mass of bone to total body mass is greatest in the rat. The results also emphasize the sensitivity of applicants' assay since it only requires five microliters of serum for a single test, a volume much less than that normally taken for clinical blood work and an amount even obtainable from children.

Quantitation of the amount of BAG-75 antigen or molecular weight=50,000 fragment can be determined separately by densitometric scanning of immunoblot membranes. Comparison with similar scans of internal standard preparations run on each gel permit normalization of peak areas in terms of the internal standard specimen. Electrophoresis with standard preparations of each antigenic form permits establishment of a standard curve from which the unknown amount of antigen can be extrapolated.

As mentioned earlier, once BAG-75 specific antibodies are produced, it will be possible to carry out more conventional ELISA assays or RIA assays to quantitate serum antigens. In that case, BAG-75 will be determined directly, while molecular weight 50,000 fragment would be determined as the difference of two separate assay results on the same serum [(total antigen determined with present anti-peptide antibody) minus (BAG-75 content determined with specific antibody)].

Alternatively, if Mr=50,000 fragment specific monoclonal antibodies are available, these antibodies can be used directly to detect and analyze this fragment selectively in ELISA assays of whole tests sera.

Figure 6:
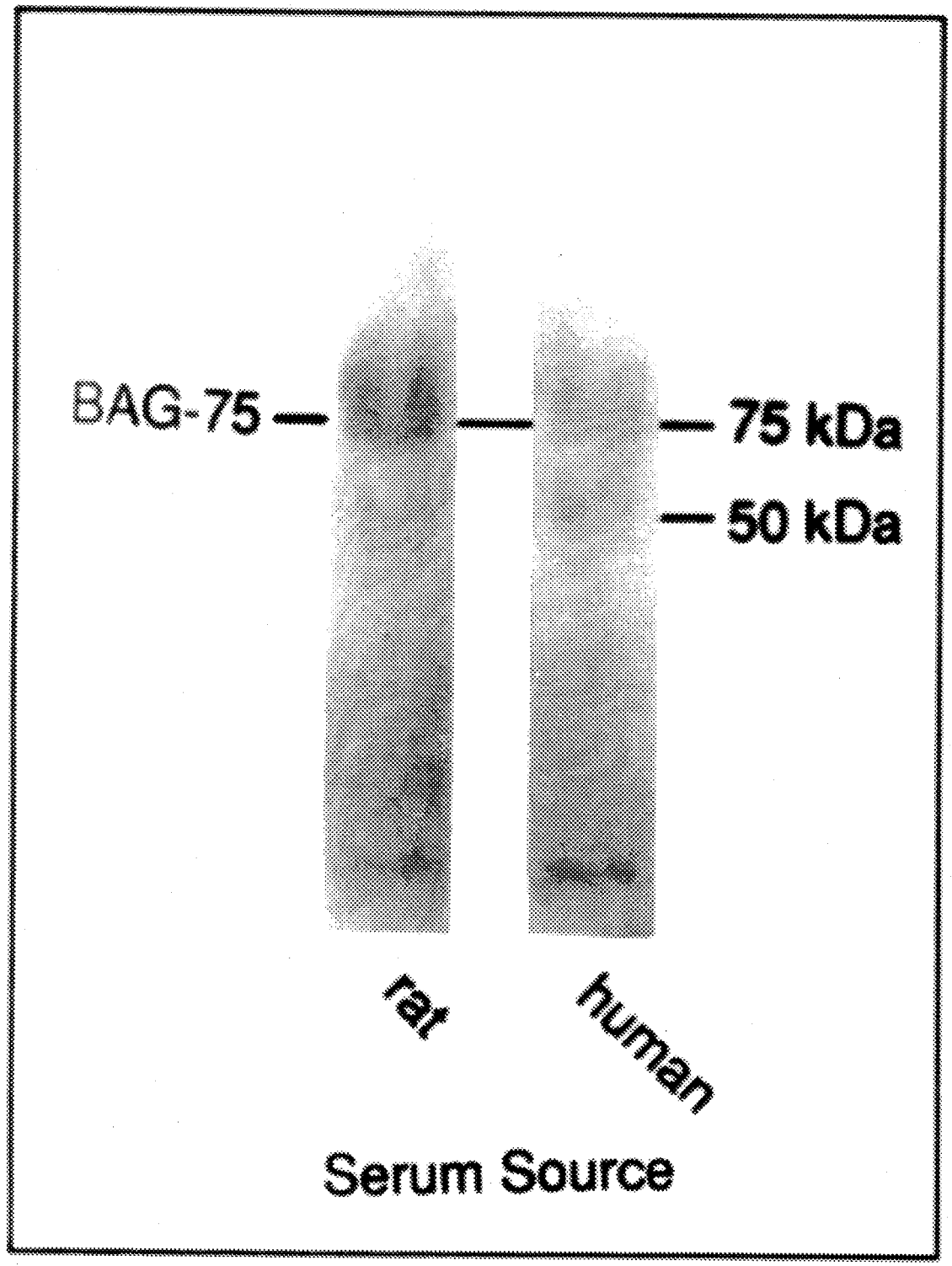

Antibodies Against Rat BAG-75 Peptide #3-13 Detect Human BAG-75 and Molecular Weight=50,000 Fragment Forms in Serum Having shown the presence of BAG-75 antigens in rat serum, applicants investigated whether the antibody would recognize antigen in human serum. A female donor (age 21) donated serum. 2 and 5 microliters were electrophoresed and transferred to nitrocellulose membrane, along with a rat serum positive control, as described earlier. As shown in FIG. 6, two bands of immunoreactivity were observed in the human serum. The bands corresponded to human BAG-75 (molecular weight 75,000) and molecular weight 50,000 fragment. The intensity of staining for BAG-75 is less for 5 microliters of human serum than that for rat serum. The reason is that human serum contains more of molecular weight 50,000 fragment and human BAG-75 antigens may not react with the antibodies with the same affinity as the rat protein.

These findings demonstrate a) that BAG-75 and molecular weight=50,000 fragment are not restricted to rat tissues; b) that antibodies against rat BAG-75 cross-react well with the human protein; and c) that an immunoassay for BAG-75 antigens in human serum is straightforward and based directly upon applicants' experiences with the rat thereby connecting the rat data to human data.

Serum of Osteosarcoma Bearing Rats is Enriched in BAG-75 (Molecular Weight=75,000)

Figure 7:
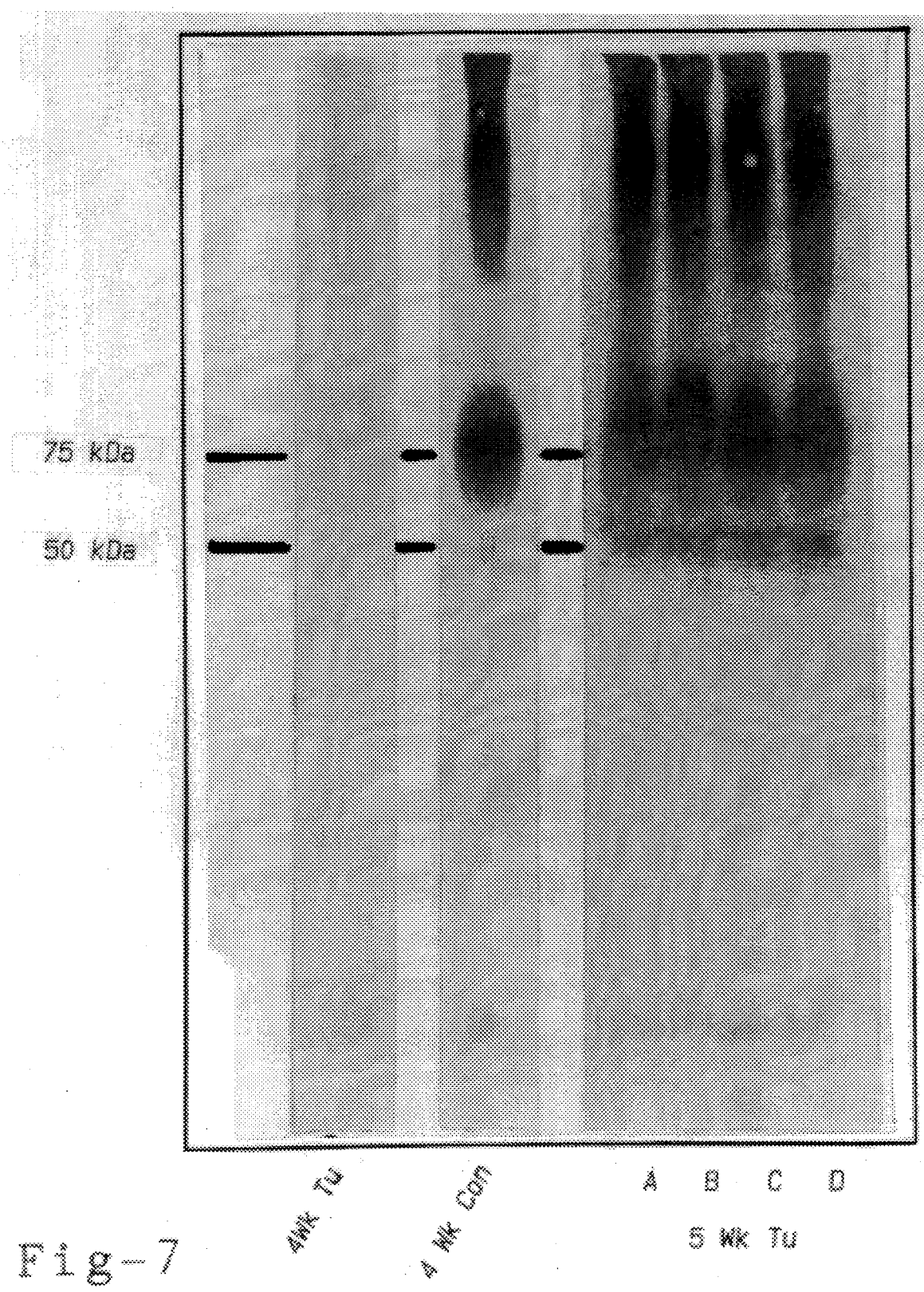

To evaluate the efficacy of applicants' immunoassay in the evaluation of serum samples from rats bearing bone tumors, littermates were injected in hindquarters with cultured rat osteosarcoma cells (line ROS 17/2.8). Under these conditions, tumors form and progress rapidly, leading to death after 5–6 weeks if animals are not killed earlier. Four and five weeks later, blood samples were taken from control and tumor bearing rats. The resultant sera were subjected to the electrophoresis, transfered to nitrocellulose membrane and reacted with anti-peptide antibodies (FIG. 7). Serum samples from tumor bearing animals contain much more immunoreactivity for BAG-75 (molecular weight=75,000) than that for the control. Strong immunostaining is found further up in tumor lanes and likely represents aggregates of BAG-75 with serum proteins or with itself. It was estimated that the BAG-75 antigen content of 5 week tumor sera is 80 ug/ml or at least 10-fold higher than age-matched non-tumor control shown. Surprisingly, total serum alkaline phosphatase activity (done by Clinical Chemistry, Truman Med. Ctr.) in the same samples increased only 30%: 72 (4 week control); 62 (4 week tumor); 95, 103, 97,90 (5 week tumor). Alkaline phosphatase has previously been used as a marker of osteosarcoma presence or of bone metabolism in general. The great elevation in BAG-75 antigen level resulting from the presence of a transplantable bone tumor in these rats suggests that the immunoassay may have validity in the diagnosis and monitoring of treatment of human patients with bone tumors.

Ovariectomy of Rats Causes Rapid 3-Fold Elevation In Serum of Molecular Weight=50,000 Fragment of BAG-75

[Samples provided by Dr. C. Frolik, E. Lilly Research Labs., for the applicant's lab to analyze]. The purpose of the pilot study was to determine if the level of BAG-75, or its fragment, was changed within 5 weeks of ovariectomy. Twelve young adult rats were ovariectomized; six were then injected with 30 ug/kg 17-beta-estradiol subcutaneously daily. Untreated, age-matched female rats served as controls. Serum samples were obtained from all rats 35 days after surgery; shipped frozen to applicant; and analyzed in blinded fashion with anti-peptide #3-13 antibodies as described above. Ten microliters of serum were applied to 12×14 cm gels with thin gel lanes and processed. Under these conditions of higher loading, serum albumin competes effectively with BAG-75 for binding to the membrane and only the molecular weight=50,000 fragment band is detected. The immunostained band was scanned with a densitometer and integrating recorder. All eighteen samples were analyzed together on the same gel to reduce interblot variability.

Findings were confirmed in duplicate runs. Fragment band areas are plotted versus group identity in FIG. 8 (the sample code was broken by Dr. C. Frolik on May 4, 1990).

Figure 8:
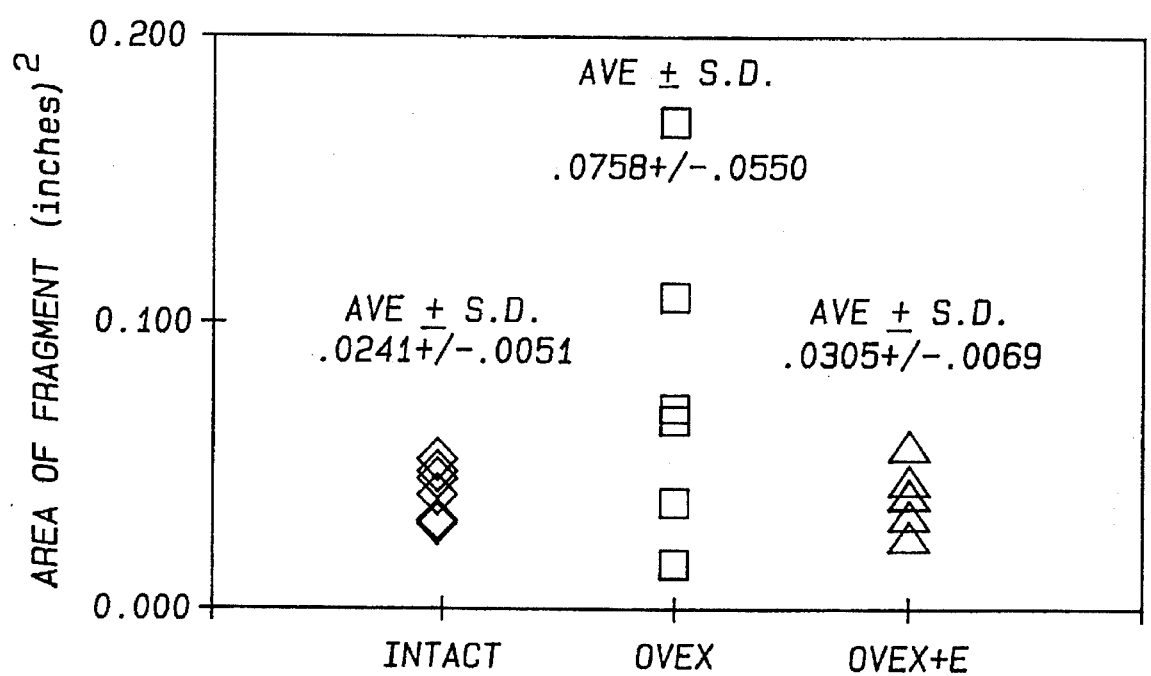

The results show a dramatic 300% average increase in serum concentration of molecular weight 50,000 fragment of BAG-75 only five weeks after ovariectomy. This change is statistically significant at a greater than 2.5% confidence limit using the Student t-test. Also apparent is that estrogen supplementation after ovariectomy prevented this increase (FIG. 8). Comparison of serum osteocalcin levels (determined by Dr. C. Frolik, Lilly) with those for BAG-75 fragment show that: a) the degree of change observed with osteocalcin was much smaller (only 27% vs. 300%); and, b) there is no obvious correlation of osteocalcin level with that for molecular weight=50,000 fragment (not shown). Given the present primacy of the osteocalcin immunoassay in the bone field for monitoring metabolic bone diseases, these findings suggest that the BAG-75 immunoassay may be applicable to diagnosis and to monitoring osteoporosis patients.

The results shown in FIG. 8 provide evidence that the serum level of the Mr=50 kDa fragment of bone acidic glycoprotein-75 rises an average of 3-fold within 35 days of ovariectomy in the rat. The six ovariectomized rats of the experiment were found to lose an average of 20% of their bone mass in the distal metaphyseal region of long bones. To follow up on this observation, the tibial bones from these same intact, ovariectomized, and ovariectomized rats supplemented daily with estrogen were analyzed to determine whether the quantity of Mr=50 kDa fragment of bone acidic glycoprotein-75 was changed in ovariectomized versus intact bone (the first time anyone has tried to address this question).

Figure 9:
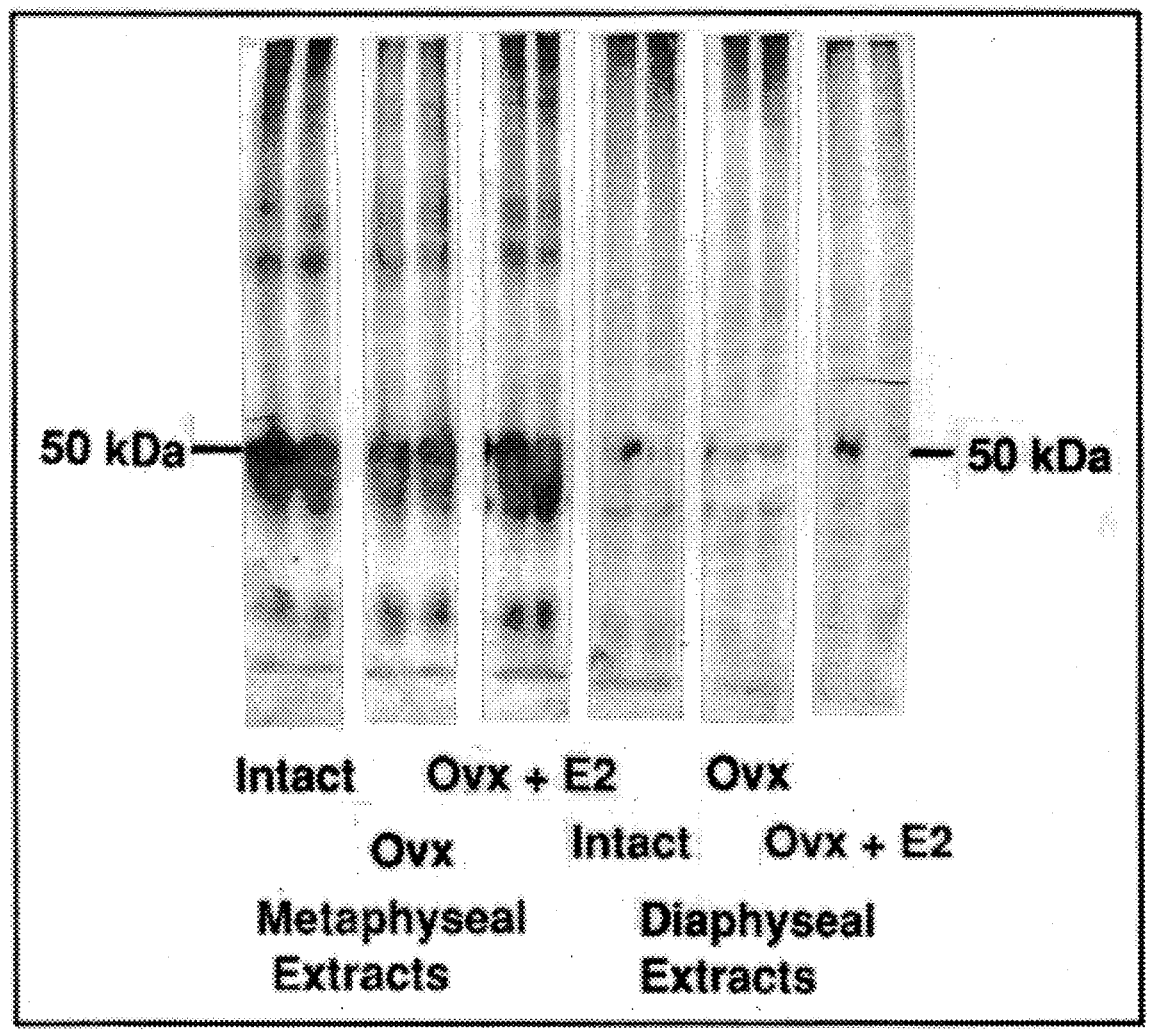
FIG. 9 is an analysis of the Mr=50 kDa fragment concentration in extracts of metaphyseal and diaphyseal rat tibial bone (detection with anti-BAG-75 protein antibodies)
Figure 10:
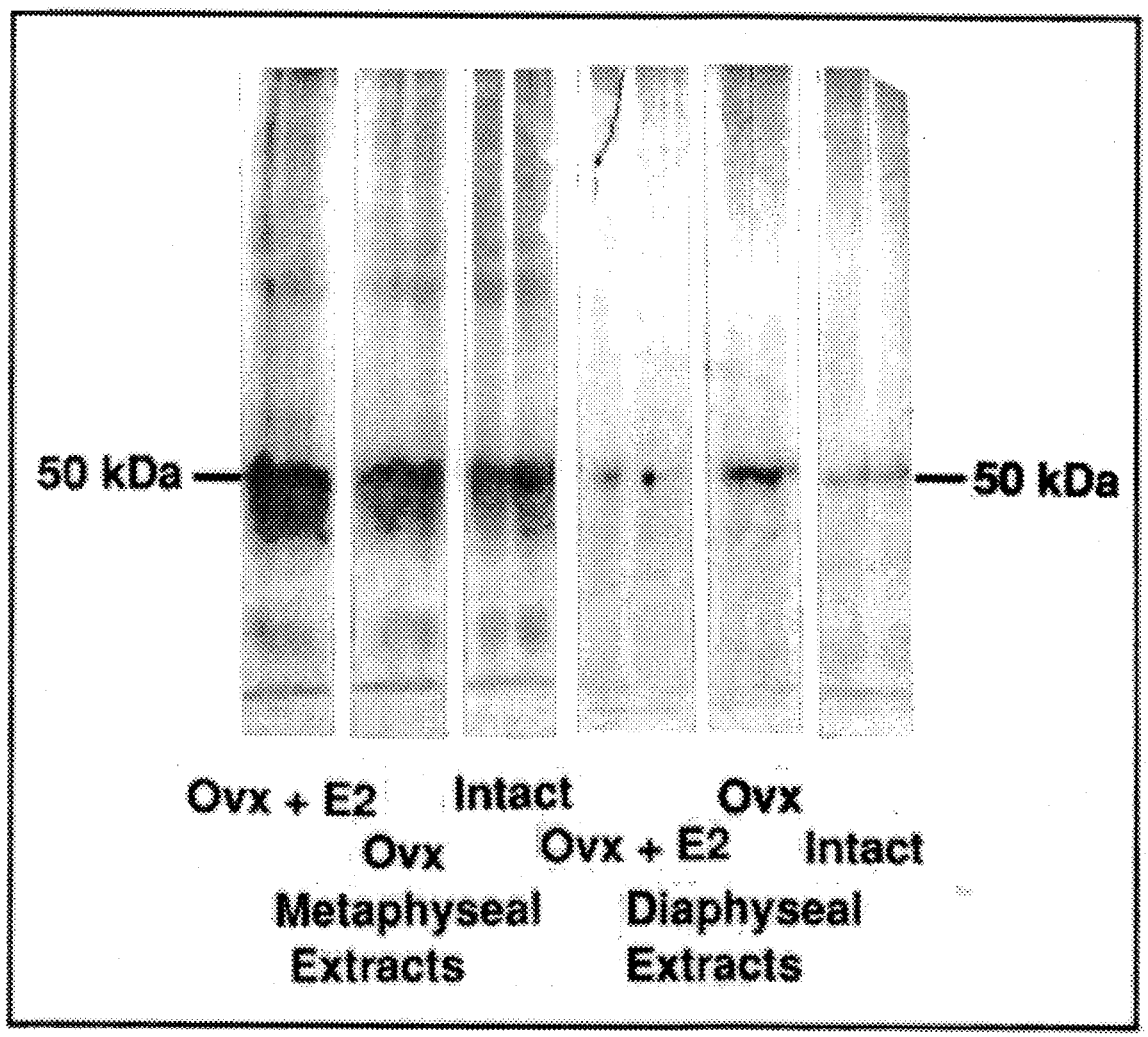
FIG. 10 is an analysis of the Mr=50 kDa fragment concentration in extracts of metaphyseal and diaphyseal rat tibial bone (detection with anti-BAG-75 peptide #3-13 antibodies)
Figure 11:
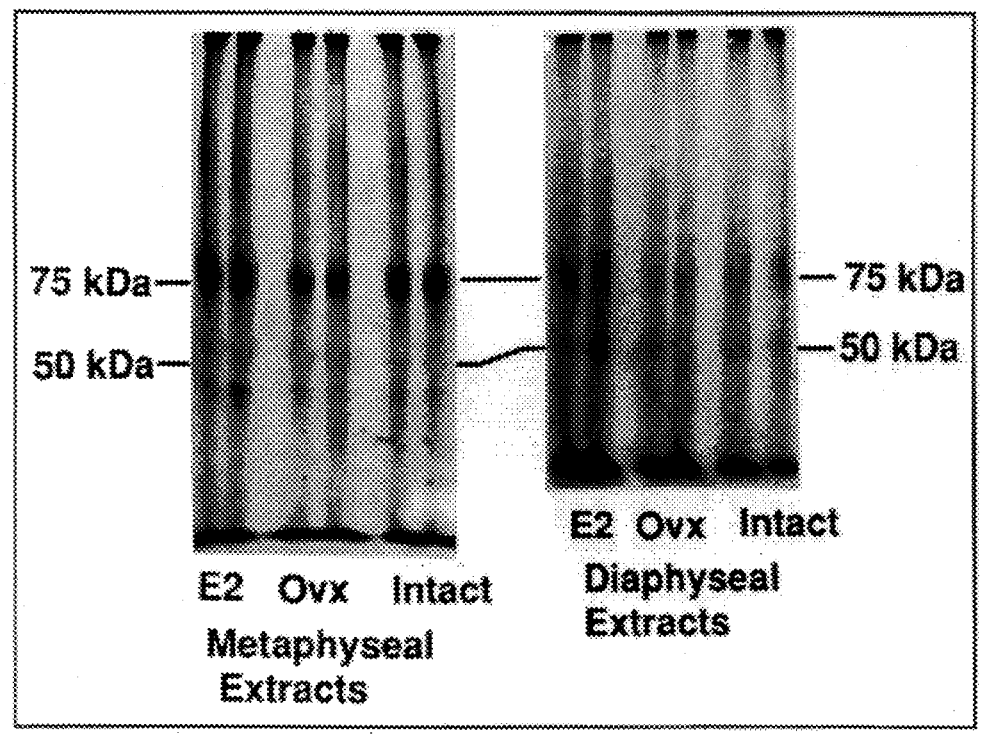
FIG. 11 shows stains-All™ staining for acidic proteins in extracts of metaphyseal and diaphyseal tibial bone.

The bones (pooled from three animals) were first dissected into metaphyseal and diaphyseal regions; metaphyseal region was operationally defined as the terminal 15% of the length of each tibia and also contains the growth plate. The bone was powdered and the bone powder extracted sequentially with 4M guanidine-HCl and then 4M guanidine-HCl/0.5M EDTA. The extracts were analyzed by SDS-polyacrylamide gel electrophoresis and Western blotting onto nitrocellulose membranes as described above. Individual samples were adjusted first to a common weight ratio based upon the initial dried bone mass. Two antibodies were used: anti-BAG-75 protein antibodies (FIG. 9) and anti-#3-13 BAG-75 peptide antibodies (FIG. 10). Total G/E bone extracts were electrophoresed on SDS-gels and eletroblotted prior to immunodetection with anti-BAG-75 antibodies. Samples were normalized to a common weight of bone extracted. It is very apparent that the Mr=50 kDa fragment is enriched in metaphyseal bone. No differences were observed among metaphyseal extracts when ovariectomized (OVX), intact, and ovariectomized supplemented with daily estrogen (OVX+E2) samples were compared. However, these results might be expected since all samples were corrected for weight of bone extracted. A similar finding was obtained with either antibody preparation (FIGS. 9 and 10). Thus, metaphyseal region is concluded to contain much more Mr=50 kDa fragment than that for the diaphyseal region. These observations suggest that the Mr=50 kDa fragment found in serum may be derived from metaphyseal bone. However, this cannot be proved definitely without further kinetic studies. Identical gels were stained with Stains All™ dye to stain acidic bone proteins (including bone acidic glycoprotein-75 and its Mr=50 kDa fragment) (FIG. 11).

The most striking finding was that the content of Mr=50 kDa fragment in the G/E extract from rat metaphyseal region was dramatically greater (>10X) than that for diaphyseal region. Bone acidic glycoprotein-75 itself is not seen on these blots because its acidic character necessitates use of cationic nylon membranes for detection. Second, no major difference was observed among the concentration of Mr=50 kDa fragment in metaphyseal region extracts from intact, ovariectomized, and ovariectomized rats receiving daily estrogen supplements. This may be expected, since the samples were normalized to a common bone mass equivalent prior to electrophoresis. Thus, although there was a 20% loss of bone mass in the ovariectomized metaphyseal region, the remaining tissue appears to have the same level of Mr=50 kDa fragment as intact bone. Third, a 2–3 fold increase in Mr=50 kDa fragment concentration was detected in the diaphyseal extract from ovariectomized rats as compared with that for intact or from ovariectomized rats supplemented with daily estrogen (30 ug/kg). Finally, the Stains All™ stained extracts showed that acidic protein components were present in both the metaphyseal and diaphyseal region G/E extracts, and, a general absence of acidic protein components in the diaphyseal region extracts did not appear to be the explanation for the large enrichment of BAG-75 antigens in the metaphyseal region.

The potential significance of the findings are two-fold. 1) The Mr=50 kDa fragment is present in much higher concentration in metaphyseal region than in diaphyseal region. The weight of metaphyseal tissue was about 4-times greater than that of diaphyseal tissue here. 2) It is reasonable to propose that the Mr=50 kDa fragments which contribute to the rise in serum level after ovariectomy are derived from the metaphyseal regions of long bones which are also the site of major bone mass loss in estrogen deficiency. The implication of this work is that the immunoassay disclosed herein is applicable to analysis of bone turnover in osteoporotic patients.

Analysis of Mr=50 kDa fragment in Sera from Osteopetrotic Rats and Normal Littermates.

To understand whether Mr=50 kDa fragment levels reflect bone formation, bone resporption, or both processes, a study of osteopetrotic rodent strains was conducted.

Osteopetrosis is an autosomal recessive disease marked by decreased or absent osteoclastic activity, although abnormal osteoblastic function is also frequently observed also. Osteoclasts are the cells responsible for bone resorption or degradation in situations of normal and altered bone turnover. The clinical manifestations of osteoclastic hypofunction are varied, however, all osteopetrotic patients show a progressive skeletal sclerosis.

Analysis of three rodent osteopetrotic strains with different phenotypes (ia, incisor absent; op, osteopetrotic, and tl toothless was performed to determine whether the level of Mr=50 kDa fragment in serum was changed, ie., a decrease would suggest that Mr=50 kDa fragment is formed during resorption of bone.

Rodent sera from 10 day (n=2–4/mutant) and six week old mutants (n=1–3/mutant) and their normal littermates (NLM) were subjected to Western blotting method. Antigenic bands were detected with primary anti-BAG-75 peptide #3-13 antibodies and alkaline phosphatase conjugated anti-rabbit antibodies, and stained bands quantitated by densitometry at 500 nm. Incisor absent mutants (ia) have 60% normal levels of osteoclastic function, and excavate a marrow cavity. Unique to this mutant is a 2–3-fold increase in osteoclast cell numbers; histologic studies of ia osteoclasts show inactive cells without a ruffled border membrane that are incapable of secreting acid hydrolyases. Op mutants have a partial marrow cavity and, like the ia mutants are cureable by transplantation of normal spleen and bone marrow cells. Toothless mutants (tl), like op mutants, have decreased numbers of osteoclasts, have severly diminished osteoclastic functional capacity (less than 5% of normal), do not form a marrow cavity, and are not cured by stem cell transplantation. The Mr=50 kDa fragment levels in the 10 day old mutants were determined in this study and found to be not significantly different from that of NLM [ia, 102%±36; op, 106%±16; tl, 113%±20 of NLM level]. In contrast, samples of six week old ia, op, and tl numbers of mutants were found to be 96, 82 and 72% of NLM serum levels, respectively. Small numbers of mutants and NLM available for study did not permit extensive statistical analysis of the latter samples, but the trends observed correlate directly with the overall osteoclastic activity expressed in rodent mutants.

Recent work shows that macrophage colony stimulating factor (M-CSF) injections into tl mutant rats was able to "cure" the osteoclastic defect present in these animals, ie., a marrow cavity was subsequently excavated. As a result, sera was analyzed from treated and untreated tl mutants in a second study. It was found that tl mutants treated with M-CSF were not different than untreated tl mutants with respect to the level of Mr=50 kDa fragment present in their sera [79% ±13 of NLM for untreated tl mutant and 71%=/−22 of NLM for treated tl mutants]. Treatment was either for 28 or 44 days. The tl values are similar to the 72% of NLM control observed in the first part of our study.

Figure 12:
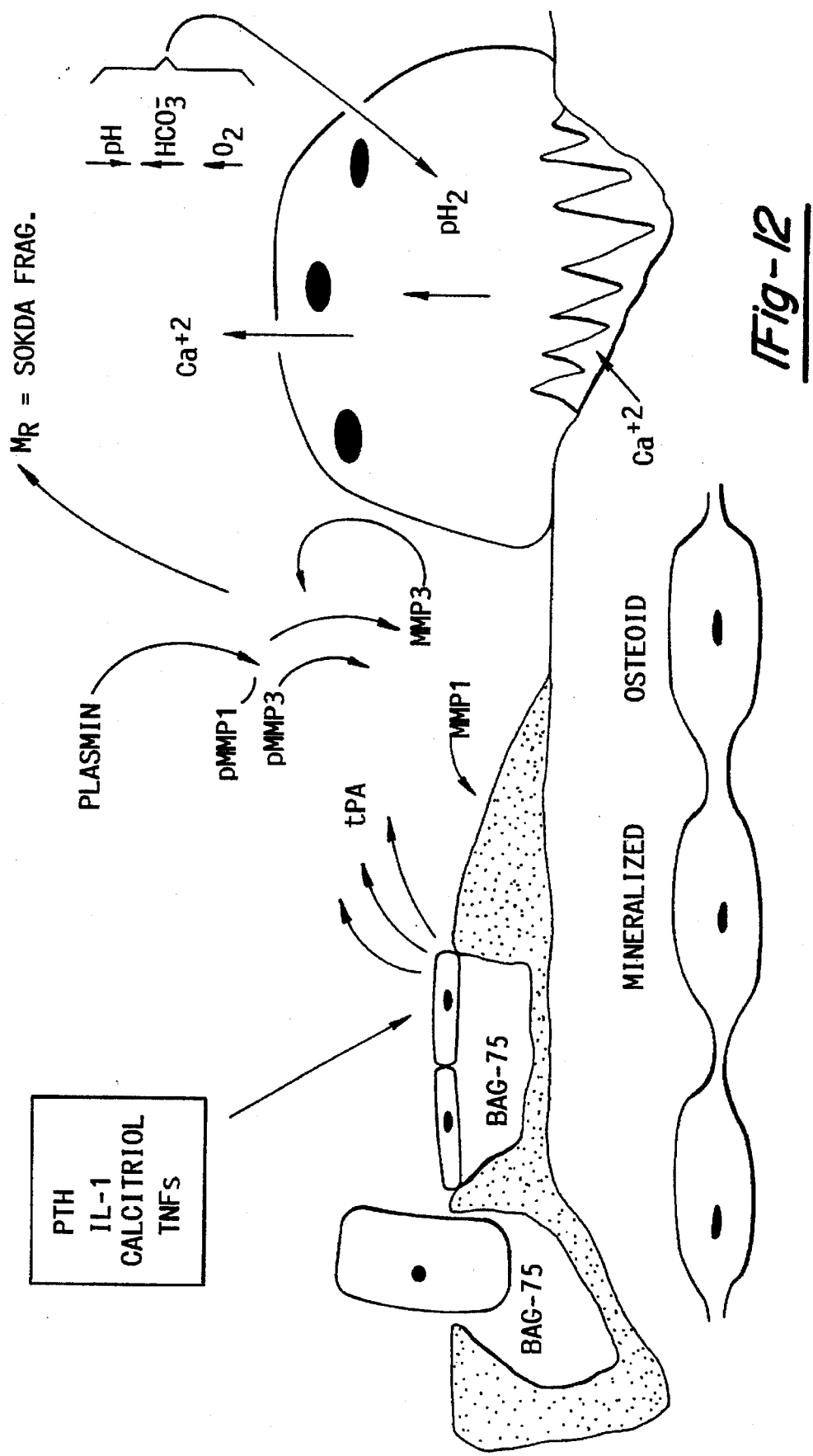
FIG. 12 is a model of bone turnover which involves proteolytic removal of unmineralized osteoid from bone surfaces prior to osteoclastic resorption.

Since a surge of osteoclast-mediated resorption would be expected to produce an increase in Mr=50 kDa fragment, it was first concluded that the Mr=50 kDa fragment of BAG-75 found in serum is not produced by cells of osteoclastic lineage, which respond to M-CSF. Osteoblastic cells are of a different cell linage than osteoclasts and do not respond directly to M-CSF. Thus, the Mr=50 kDa fragment may be produced by metalloproteinases secreted by osteoblastic lining cells in bone. In this way, the lowered Mr=50 kDA fragment level observed in osteopetrotic mutants would be rationalized in terms of a coincident and "uncured" decrease in either BAG-75 secretion and/or fragmentation by osteoblast-derived metalloproteases. Chambers and others have shown that while osteoclasts will adhere to osteoid or unmineralized bone surfaces, resorption does not proceed until the unmineralized layer is first removed by proteases such as collagenase and stromelysin. Collagenase and stromelysin are products of certain populations of osteoblastic cells whose regulated secretion represents a common pathway for the action of resorption stimulators, including calcitriol, interleukin-1, and parathyroid hormone. Since other work from applicant's laboratory has shown that a Mr=50 kDa fragment can be produced by incubation of BAG-75 with collagenase or stromelysin, it is proposed (see model in FIG. 12) that lining cells under calcitropic hormone control, secrete collagenase and stromelysin which remove the unmineralized osteoid layer of bone surfaces, and in the process, produce the Mr=50 kDa fragment of BAG-75; which is released to serum. Morphologically, increased bone resorption accompanies injection of rats with M-CSF. Since this treatement is unphysiologic, it is possible that the mechanism of resprption in "cured" tl rats is not identical with that occurring normally, and thus Mr=50,000 fragment levels remain unchanged.

In summary, the above data shows that Mr=50 kDa fragment serum levels go up 3-fold in rats that have accelerated bone turnover (after ovariectomy) and go down in rough proportion to heriditary losses in osteoclast-mediated resorption (in osteopetrotic mutants). The metaphyseal region of long bones was shown to be enriched in Mr=50,000 fragment; this same region is subject to a dramatic loss in mass following ovariectomy. These findings support the potential utility of immunoanalysis of Mr=50 kDa fragment to monitor changes in bone turnover of patients.

The above demonstrates that the present invention provides a simple analytical method to determine the size and amount of BAG-75 protein and metabolic fragment present in serum samples. The test is also applicable to analysis of synovial fluid. The data indicates that it is highly likely that the present invention can be used in the detection of various disease states and monitoring response to therapy.

Further, it can be concluded that the anti-peptide #3-13 and anti-BAG-75 protein sera both recognize BAG-75 antigen of 75,000 of molecular weight and an apparent fragment or biosynthetic intermediate of 50,000 molecular weight. The latter represents the major antigenic form in bone extracts. A fragment-precursor relationship is suggested from the fact that closely spaced doublet polypeptides of the 50,000 molecular weight fragment can be produced by proteolysis upon long term storage of purified BAG-75 at 4° C. The identity of the immunoreactive 50,000 molecular weight proteins found in bone and in serum with these fragments is suggested by a similarity in size and reactivity with anti-BAG-75 protein antibodies.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCE 8

1. Gorski, J. P. et al, (1988) *J. Biol. Chem.* 263, 15938–15945.
2. Hauschka, P. V. et al., (1975) *Proc. Natl. Acad. Sci. U.S.A.* 72, 3925–3929
3. Price, P. A. et al., (1976) *Proc. Natl. Acad. Sci. U.S.A.* 73, 1447–1451
4. Termine, J. D. et al., (1981) *Cell* 26, 99–105
5. Franzen, A. et al., (1985) in *The Chemistry and Biology of Mineralized Tissues* (Butler, W. T., ed) pp. 132–141, EBSCO Media, Birmingham, Ala.
6. Fisher, L. W. et al., (1987) *J. Biol. Chem.* 262, 9702–9708
7. Uchyama, A. et al., (1986) *Biochemistry* 25, 7572–7583.
8. Fisher, L. W. et al., (1983) *J. Biol Chem.* 258, 12733–12727
9. Franzen, A. et al., (1985) *Biochem J.* 232, 715–724
10. Prince, C. W. et al., (1987) *J. Biol. Chem.* 262, 2900–2907
11. Boskey, A. L. (1981) *Clin. Orthop.* 157, 165–196
12. Termine, J. D. (1980) *J. Biol. Chem.* 255, 9760–9768
13. Linde., A. et al., (1980) *J. Biol. Chem.* 255, 5931–5942
14. Laemmli, U. K. (1970) *Nature* 227, 680–685
15. Campbell, K. P. et al., (1983) *J. Biol. Chem.* 258, 11267–11273

16. Shinnick, T. M. et al., (1983) *Annu. Rev. Microbiol.* 37, 425–446

17. Fisher, L. W. et al., (1987) *J. Biol. Chem.* 262, 9702–9708

What is claimed is:

1. A method of detecting bone acidic glycoprotein-75 and its 50,000 MW fragment in a test sample, said method comprising:

(a) incubating a serum or synovial fluid sample with an antibody that specifically binds to bone acidic glycoprotein-75 and its 50,000 MW fragment, thereby forming antigen/antibody complexes; and (b) detecting any bone acidic glycoprotein/antibody and 50,000 MW fragment/antibody complexes as an indication of the presence of bone acidic glycoprotein-75 and its 50,000 MW fragment in the test sample.

2. The method of claim 1, wherein said detecting step comprises:

(a) incubating said complexes with an anti-IgG antibody conjugated to an enzyme, wherein said enzyme is either horseradish peroxidase or alkaline phosphatase, thereby forming enzyme-labelled complexes;

(b) incubating said enzyme-labelled complexes with a colorimetric substrate specific for said enzyme; and (c) detecting said enzyme-labelled complexes by measuring any resulting color formation.

3. A method of detecting bone acidic glycoprotein-75 and its 50,000 MW fragment in a test sample, said method comprising:

(a) electrophoretically separating a serum or synovial fluid sample to form a separated sample;

(b) electrophoretically transferring said separated sample to a cationic nylon membrane to form a transferred sample;

(c) incubating said transferred sample with an antibody that specifically binds to bone acidic glycoprotein-75 and its 50,000 MW fragment, thereby forming antigen/antibody complexes; and (d) detecting any bone acidic glycoprotein/antibody and 50,000 MW fragment/antibody complexes as an indication of the presence of bone acidic glycoprotein-75 and its 50,000 MW fragment in said test sample.

4. The method of claim 3, wherein said detecting step comprises:

(a) incubating said complexes with an anti-IgG antibody conjugated to an enzyme, wherein said enzyme is either horseradish peroxidase or alkaline phosphatase, thereby forming enzyme-labelled complexes;

(b) incubating said enzyme-labelled complexes with a colorimetric substrate specific for said enzyme; and (c) detecting said enzyme-labelled complexes by measuring any resulting color formation.

5. The method of claim 4, wherein the detecting step further comprises:

(d) separately quantitating the amount of bone acidic glycoprotein-75 and its 50,000 MW fragment by densitometric scanning.

* * * * *